United States Patent

Bargain

[11] 3,966,531
[45] June 29, 1976

[54] COMPOSITIONS CONTAINING SILANES POSSESSING IMIDE GROUPS

[75] Inventor: Michel Bargain, Lyon, France

[73] Assignee: Rhone-Poulenc Industries, Paris, France

[22] Filed: Feb. 3, 1975

[21] Appl. No.: 546,447

[30] Foreign Application Priority Data
Feb. 5, 1974  France .................. 74.03799

[52] U.S. Cl. .................. 156/329; 156/331; 260/78 UA; 260/326 E; 260/78 SC; 260/448.2 N; 427/387; 427/407; 428/447; 428/448

[51] Int. Cl.² .................. C09J 1/00; C09J 5/00

[58] Field of Search .................. 156/331, 110 A, 329, 156/326, 325; 117/161 P, 161 ZA, 126 CN, 124 F, 135.1; 161/193, 207, 206, 208; 260/326.5 A, 326.26, 326 E, 326.44, 326.25, 326.5 J, 824 R, 25, 78 UA, 78 SC, 448.2 N, 88.3 R, 448.2 E, 448.2 A; 106/287 SB; 428/446, 450, 447, 452, 448, 429, 435; 427/387, 407

[56] References Cited
UNITED STATES PATENTS

| | | | |
|---|---|---|---|
| 2,721,873 | 10/1955 | MacKenzie et al. | 106/287 SB |
| 2,818,405 | 12/1957 | Kovacic | 260/78 UA |
| 3,185,704 | 5/1965 | Kahn et al. | 260/326.44 |
| 3,379,607 | 4/1968 | Foster et al. | 161/207 |
| 3,499,870 | 3/1970 | Hadlock et al. | 117/135.1 |
| 3,562,223 | 2/1971 | Bargain et al. | 260/78 UA |
| 3,717,615 | 2/1973 | Holub et al. | 117/161 P |
| 3,759,779 | 9/1973 | Jumas | 260/78 UA |

Primary Examiner—William A. Powell
Assistant Examiner—J. J. Gallagher
Attorney, Agent, or Firm—Stevens, Davis, Miller & Mosher

[57] ABSTRACT

Compositions are prepared by reacting one mol of a bis-imide of the formula:

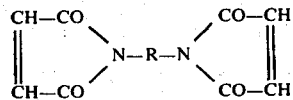

with at least one mol of an amino-silane of the formula:

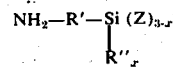

in which R represents a divalent hydrocarbon radical with 2 to 20 carbon atoms which is free from unsaturated bonds other than aromatic bonds, a divalent mono- or bis-heterocyclic radical with 2 to 10 carbon atoms, or a divalent organic radical with 4 to 20 carbon atoms which consists of more than one said divalent hydrocarbon radical bonded to one another via —O—, —S—, —CO— or —SO$_2$—, R' represents a divalent hydrocarbon radical with 1 to 20 carbon atoms or a divalent radical with 4 to 20 carbon atoms which consists of more than one hydrocarbon radical bonded to one another via —NH— or —O—, Z represents a hydrolysable group, R'' represents a monovalent radical with 1 to 6 carbon atoms and $x$ is 0 or 1. These compositions are particularly useful, especially as solutions, as undercoats for adhering organopolysiloxane compositions to a variety of substrates.

11 Claims, No Drawings

COMPOSITIONS CONTAINING SILANES POSSESSING IMIDE GROUPS

The present invention relates to compositions based on organosilicon compounds possessing imide groups.

The compositions of the present invention generally comprise a compound of the formula:

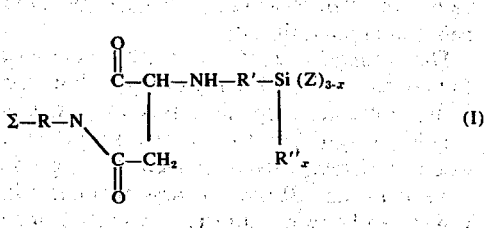

(I)

in which the symbol R represents a hydrocarbon radical with 2 to 20 carbon atoms and which is free from unsaturated bonds other than aromatic bonds, a mono- or bis-heterocyclic radical with 2 to 10 carbon atoms, or an organic radical with 4 to 20 carbon atoms which consists of several hydrocarbon radicals defined above, bonded to one another via —O—, —S—, —CO— or —SO$_2$—, the symbol R' represents a hydrocarbon radical with 1 to 20 carbon atoms or a radical with 4 to 20 carbon atoms which consists of hydrocarbon radicals bonded via —NH— or —O—, the symbol Z represents a hydrolysable group, the symbol R" represents a monovalent radical with 1 to 6 carbon atoms, $x$ is equal to 0 or 1, and the symbol Σ represents a

(I')

radical or a

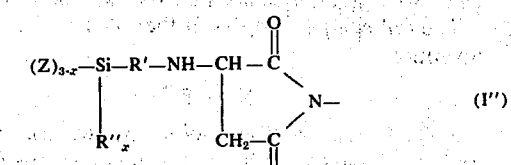

(I")

radical, wherein R', R" and Z are as defined above.

The hydrocarbon radicals represented by the symbol R can be, for example, a linear or branched alkylene radical with 2 to 12 carbon atoms, a phenylene radical, a cyclohexylene radical, a naphthylene radical, a biphenylene radical, a xylylene radical, or a radical of the formula:

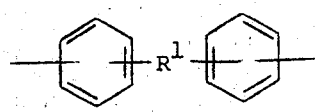

in which the symbol R$^1$ denotes an alkylene radical with 1 to 3 carbon atoms optionally substituted by a phenyl radical. The phenylene radicals can be substituted by groups such as —CH$_3$ or —OCH$_3$, or by a chlorine atom. When the symbol R represents a heterocyclic radical, it can be, for example, one of the radicals of the formulae:

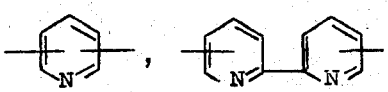

and

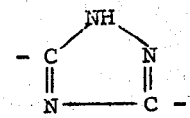

The hydrocarbon radicals represented by the symbol R' can be chosen from amongst the radicals mentioned above for the symbol R.

Typical hydrolysable groups represented by the symbol Z include the groups of the formulae —OG,

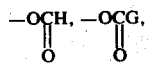

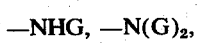

—ON=CHG, —ON=C(G)$_2$ and —ON(G)$_2$, in which each of the symbols G, which may be identical or different, represents a monovalent hydrocarbon radical containing at most 15 carbon atoms, or two G radicals together form a divalent radical optionally containing a hetero-atom such as oxygen. The symbols G represent, in particular, a methyl, ethyl, propyl, hexyl, cyclohexenyl, cyclohexyl, phenyl, benzyl or tolyl radical, or two symbols G form a divalent radical such as —(CH$_2$)$_n$— or —(CH$_2$)$_n$ — O(CH$_2$)$_n$—, wherein $n$ is an integer from, for example, 1 to 5.

The symbol R" represents in particular, a radical with 1 to 6 carbon atoms mentioned above for the symbol G, or one of these radicals substituted by a halogen atom or a cyano group.

The products of formula (I) can be prepared by reacting one mol of a bis-imide of the formula:

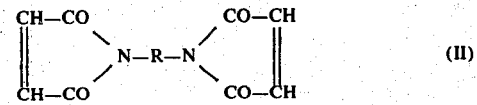

(II)

with at least one mol of an amino-silane of the formula:

(III)

in which the symbols R, R', R" and Z are as defined above.

Specific examples of bis-maleimides of formula (II) include: N,N'-ethylene-bis-maleimide, N,N'-hexamethylenebis-maleimide, N,N'-dodecamethylene-bis-maleimide, N,N'-(2,2,4-trimethyl-hexamethylene)-bis-maleimide, 1,2-bis-(2-maleimido-ethoxy)-ethane, 1,3-bis-(3-maleimido-propoxy)propane, N,N'-meta-phenylene-bis-maleimide, N,N'-para-phenylene-bis-maleimide, N,N'-4,4'-diphenylmethane-bis-maleimide, N,N'-4,4'-(diphenyl ether)-bis-maleimide, N,N'-4,4'-(diphenyl sulphide)-bis-maleimide, N,N'-4,4'-diphenylsulphone-bis-maleimide, N,N'-4,4'-benzophenone-bis-maleimide, N,N'-4,4'-dicyclohexylmethane-bis-maleimide, N,N'-pyridine-2,6-diyl-bis-maleimide, N,N'-α,α'-4,4'-dimethylenecyclohexanebis-maleimide, N,N'-meta-xylylene-bis-maleimide, N,N'-para-xylylene-bis-maleimide, N,N'-4,4'-(1,1-diphenyl-propane)-bis-maleimide, N,N'-4,4'-(1,1,1-triphenyl-ethane)-bis-maleimide, N,N'-4,4'-triphenylmethane-bis-maleimide, N,N'-3,5-(1,2,4-triazole)-bis-maleimide, N,N'-(1,5-naphthylene)-bis-maleimide, N,N'-(1,4-cyclohexylene)-bis-maleimide, N,N'-(5-methyl-1,3-phenylene)-bis-maleimide and N,N'-(5-methoxy-1,3-phenylene)-bis-maleimide.

These bis-maleimides can be prepared as described in, for example, U.S. Pat. No. 3,018,290, British patent specification No. 1,137,592 or French Pat. No. 2,055,969.

Specific examples of amino-silanes of formula (III) include: aminomethyl-triethoxy-silane, (3-amino-propyl)triethoxy-silane, (3-amino-propyl)-methyl-diethoxy-silane, (3-amino-propyl)-phenyl-dimethoxy-silane, (4-amino-butyl)triethoxy-silane, (3-amino-2-methyl-propyl)-triethoxy-silane, (4-amino-butyl)-methyl-diethoxy-silane, (3-aminopropoxypropyl)-triethoxy-silane, (3-amino-propoxypropyl)-trimethoxy-silane, (3-amino-propoxypropyl)-methyl-diethoxysilane, (3-amino-propoxypropyl)-ethyl-diethoxy-silane, (p-aminophenyl)-triethoxy-silane, (2-amino-ethylaminomethyl)-(methoxyethoxy)-bis-(1-methyl-propylidene aminoxy)-silane and [(ω-amino-alkylamino)-alkyl]-trialkoxy-silanes, and, especially, [3-(2-amino-ethylamino)-propyl]-trimethoxysilane, [3-(3-amino-propylamino)-propyl]-triethoxy-silane, [(2-amino-ethylamino)-methyl]-triethoxy-silane and [(6-aminohexylamino)-methyl]-trimethoxy-silane.

The reaction between the bis-imide (II) and the amino-silane (III) generally takes place at a temperature from 0° to 100°C. It is advantageous to carry out this reaction in the presence of a diluent. As a general rule, the maleimide is dissolved partially or completely in a suitable solvent such as a hydrocarbon, a chlorinated aliphatic or aromatic solvent, an ester, an ether, a ketone, a nitrile or an amide, and the amino-silane is incorporated gradually. This procedure possesses the advantage that one can produce a product of formula (I) in which Σ has the desired meaning (I' or I'') depending on the molar ratio $$\frac{\text{amino-silane}}{\text{bis-imide}}$$

In general, this ratio is from 1 to 2. It is possible to use a ratio greater than 2, especially when the procedure described above is followed. Generally however, it is not necessary for this ratio to exceed 5.

Although this invention relates particularly to compositions containing products derived from a bis-imide (II), it is also possible to use a mixture containing a bis-imide (II) and, for example, up to 20 mol % of a mono-imide such as maleimide, N-alkyl- or N-aryl-maleimides or maleimides possessing acetoxy or acet-amido groups, which can be produced in the preparation of certain bis-maleimides, with the amino-silane.

The compositions according to the invention, which are generally in the form of solutions of the products of the formula (I) in a solvent which may be chosen from those mentioned above, can be used for various purposes. In particular they can be used for coating or impregnating various substrates and for preparing paints or varnishes which possess the advantage of being weather-resistant.

The compositions of this invention can also be used as undercoats for adhering organopolysiloxane elastomers, polyesters, epoxy resins or resins possessing maleimide groups, to various supports, especially wood, concrete, metals, polyethylene, glass and glass fibre materials. Resins possessing maleimide groups which can be used with such undercoats include those which are prepared from bis-maleimides (alone or as a mixture with mono-maleimides) as well as the resins prepared by reacting bis-maleimides with polyamines (described, for example, in French Pat. No. 1,555,564) or with imines (described, for example, in Belgian Pat. No. 805,817 or French Pat. No. 2,193,848). When using these compositions as adhesion layers, it is advantageous to incorporate into the compositions a curing accelerator such as an alkyl-tin salt, for example dibutyl-tin dilaurate, dibutyl-tin maleate, dimethyl-tin dilaurate or the product obtained from dibutyl-tin dilaurate and butyl titanate, generally in an amount from 0.1 to 10% by weight of the weight of the product of formula (I).

The compositions according to the present invention are particularly valuable for the manufacture of joints in the building industry, where they provide an excellent bond to dry or wet concrete, of organopolysiloxane compositions which can be vulcanised at ambient temperature in the presence of water in the liquid or vapour state. Such compositions usually contain a linear organopolysiloxane compound, generally possessing terminal hydroxyl groups, a silane, polysilane or siloxane possessing more than 2 hydrolysable groups by way of a crosslinking agent, and fillers. These compositions can also contain a catalyst such as an alkyl-tin salt.

The following Examples further illustrate the present invention.

EXAMPLE 1 a. 71.6 g of N,N'-4,4'-diphenylmethane-bis-maleimide, followed by 306 g of methylene chloride, are introduced into a one litre flask. The mixture is heated at the boiling point to dissolve the bis-maleimide, the solution is then cooled to 15°C and 88.4 g of (3-amino-propyl)-triethoxy-silane are run into it over 35 minutes.

After 2 hours 40 minutes at a temperature of between 17° and 22°C, the solution is boiled to concentrate it; 253 g of methylene chloride are thus distilled over the course of 55 minutes.

A product of the formula:

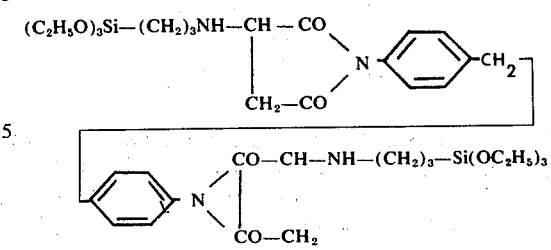

is identified in this solution, by infra-red spectrography.

b. 64.42 g of a solution comprising 8.42 g of dibutyl-tin dilaurate and 56 g of toluene are incorporated into the concentrated solution described above (213 g).

The surfaces of two concrete briquettes of dimensions 5 × 5 × 2.5 cm, previously stored for 1 week at 25°C (relative humidity; 50%) are brushed with this solution (denoted by $S_1$).

After drying for 1 hour, a second layer of the solution $S_1$ (total deposit of solution $S_1$:300 g/m$^2$) is deposited on each of the briquettes.

The second layer is left to dry for 4 hours at 25°C and the two coated briquettes are then glued by means of an organosilicon composition which can be crosslinked by the moisture in the atmosphere. This composition is based on an $\alpha,\omega$-dihydroxylic-polydimethylsiloxane oil of viscosity 500 cPo at 25°C, a silica filler (specific surface area 200 g/m$^2$) which has been treated with octamethylcyclotetrasiloxane, a crosslinking agent consisting of [bis-(ethylideneaminoxy)]-(methoxyethoxy)-methyl-silane, and a tin-based vulcanisation catalyst. The briquettes are kept together by means of an adhesive tape and are left for 6 days at 25°C exposed to the atmosphere; the adhesive tape is then removed and the combination is left exposed to the atmosphere at 25°C for a further 7 days. The strength of the gluing joint is measured by continuous stretching on a Lhomargy machine at a rate of 6 mm/minute.

It is found that the organosilicon elastomer undergoes rupture when a tensile strength of 8.0 kg/cm$^2$ is applied, the elongation being 470%. There is no detachment of the glue when the elastomer undergoes rupture (cohesive rupture).

c. Concrete briquettes of dimensions 5 × 5 × 2.5 cm are immersed in water at 25°C for 24 hours. On being removed from the water, the surfaces of the briquettes are sponged and then 2 layers of solution $S_1$ are applied (drying periods of 4 hours 30 minutes and 3 hours 15 minutes, respectively, at 25°C — total deposit 300 g/m$^2$).

Rupture of the elastomer (procedure as indicated under b) takes place with a tensile strength of 6.5 kg/cm$^2$, the elongation then being 435%. This rupture is semicohesive (part in the bulk of the elastomer, and part at the glue).

d. Dry concrete is coated with solution $S_1$, employing the following drying times (total deposit 300 g/m$^2$):
1st layer: 2 hours 10 minutes
2nd layer: 3 hours 30 minutes.

The vulcanisable composition used for gluing the concrete comprises an $\alpha,\omega$-dihydroxylic-polydimethylsiloxane oil, treated silica (see b) and methyl-triacetoxy-silane. Following the procedure as under b), it is found that semi-cohesive rupture of the organosilicon elastomer takes place with a tensile strength of 8.9 kg/cm$^2$, the elongation then being 215%.

EXAMPLE 2 a. 71.6 g of the bis-imide of Example 1 and 306 of methylene chloride are introduced into a flask, the mixture is boiled to dissolve the bis-imide (duration 23 minutes) and then cooled to 13°C; 88.4 g of (3-aminopropyl)triethoxy-silane are run in over 44 minutes, with cooling.

The mixture is then heated to the boiling point and 150 cm$^3$ of methylene chloride are distilled over the course of 40 minutes.

By applying the method described in Example 1, the same product as in Example 1 is identified in the solution.

b. 8.42 g of dibutyl-tin dilaurate are incorporated into this solution and the resulting mixture is used as an adhesion undercoat on concrete for the organosilicon composition described under 1b, following the technique described under 1b.

Cohesive rupture of the elastomer is noted at a tensile strength of 9.85 kg/cm$^2$ and an elongation of 470%.

EXAMPLE 3 a. As in Example 1, 71.6 g of the same bis-imide are dissolved in 306 g of methylene chloride; then the solution is cooled to 20°C and 132.6 g of (3-amino-propyl)-triethoxy-silane are introduced into it over 50 minutes. 130 cm$^3$ of methylene chloride are distilled over the course of 35 minutes.

The product of Example 1 is identified in the solution.

b. 10.7 g of dibutyl-tin dilaurate are added to this solution and the solution is used as an adhesion layer on concrete, following the technique described under 1b (dry concrete) and 1c (wet concrete), using the same composition.

The following results are noted:
Dry concrete: cohesive rupture of the elastomer at a tensile strength of 7.3 kg/cm$^2$, the elongation being 360%.
Wet concrete: semi-cohesive rupture of the elastomer at a tensile strength of 7.3 kg/cm$^2$, the elongation being 445%.

EXAMPLE 4 a. 71.6 g of N,N'-4,4'-diphenylmethane-bis-maleimide and 380 g of methylene chloride are introduced into a 1 l flask. The mixture is boiled in order to achieve dissolution, and then 44.2 g of (3-amino-propyl)triethoxy-silane are run in at 42°C, over the course of 10 minutes. A product of the formula:

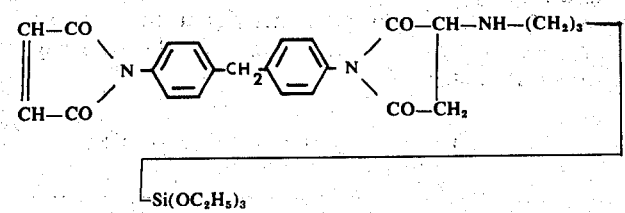

is identified in this solution. 2.9 g of dibutyl-tin dilaurate in 5 cm$^3$ of methylene chloride are added. 168 cm$^3$ of methylene chloride are then distilled over the course of 1 hour 10 minutes.

b. This solution (S₄) is used as an adhesion primer for aluminium under the following conditions: Aluminium test pieces (5 × 5 × 0.5 cm) are degreased and treated with a mixture of sulphuric and chromic acids, and are then washed with water and dried. They are coated twice with the solution (S₄), applied with a 2 hour interval between. Using the organosilicon elastomer described under 1b, cohesive rupture of the elastomer is observed at:

tensile strength: 10 kg/cm²
elongation: 450%.

c. 0.7 g of a mixture of chlorinated diphenyls, available commercially from Messrs. Ugine Kuhlmann under the tradename "Electrophenyl" is introduced into 5 g of the solution (S₄) and the resulting mixture is used for coating dry concrete as described under 1b. Cohesive rupture of the elastomer is observed at:

tensile strength: 6.1 kg/cm²
elongation: 390%.

EXAMPLE 5 a. 26.8 g of meta-phenylene-bis-maleimide are introduced into 310 g of methylene chloride and 44.2 g of (3-amino-propyl)-triethoxy-silane are run in, at 18°–19°C, over 30 minutes, into the suspension of the maleimide in methylene chloride. A homogeneous solution is obtained. A product of the formula:

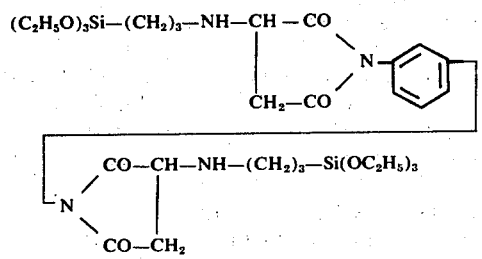

is identified in the solution.

The solution is boiled; 270 cm³ of methylene chloride are distilled over the course of 1 hour. 3.74 g of dibutyl-tin dilaurate are then added.

b. In a test involving gluing dry concrete, carried out under the conditions described under 1b, using the same composition, the following results are noted:

Semi-cohesive rupture of the elastomer at a tensile strength of 8.30 kg/cm², the elongation being 380%.

EXAMPLE 6

When using the solution described under 1a, applied as a single layer, for gluing small plates of various species of wood, and the elastomer described under 1b (working procedure as in Example 1), the following results are noted:

| Species | Tensile Strength kg/cm² | Elongation % | Type of rupture |
|---|---|---|---|
| Gaboon | 8.8 | 480 | cohesive |
| Beech | 8.4 | 490 | " |
| Oak | 7.9 | 440 | " |
| Poplar | 8.3 | 460 | 41 |
| Fir | 9.0 | 440 | " |

EXAMPLE 7

A glass fabric (weight 73.4 g/m²), which has previously been desized by heat, is impregnated with the solution as defined in Example 2, paragraph b. This solution contains the product, the formula of which is indicated in Example 1; the procedure is such that 1 g of this product is deposited per 100 g of fabric. After drying the fabric thus treated, this fabric is coated with a solution containing:

38.5 g of N-methyl-2-pyrrolidone and
31.5 g of a prepolymer prepared from N,N'-4,4'-diphenylmethane-bis-maleimide (2.5 mols) and bis-(4-aminophenyl)-methane (1 mol). The weight of prepolymer deposited is 38.8 g per 100 g of the mixture of prepolymer + glass fabric.

After drying (30 minutes at 130°C), the fabric is cut up into 15 rectangles of dimensions 9 × 8.2 cm which are stacked and placed under a press pre-heated to 120°C. A pressure of 26.5 bars is applied and the temperature is raised from 120° to 200°C over the course of 30 minutes. The laminate is removed from the press and is stoved for 18 hours at 250°C.

The flexural breaking strength (FS) and the flexural modulus (FM) are measured at 25°C, using four test pieces cut out of this laminate. FS values ranging from 44.3 to 47.1 kg/mm² (average 46.1 kg/mm²) and FM values ranging from 1,386 to 1,758 kg/mm² (average 1,576 kg/mm²) are obtained.

I claim:

1. Process for the preparation of a composition based on imide-group containing organosilicon compound which comprises reacting one mol of a bis-imide of the formula:

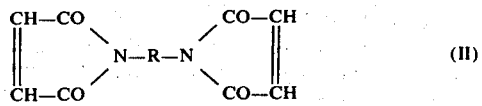

with at least one mole of an amino-silane of the formula:

in which R represents a divalent hydrocarbon radical with 2 to 20 carbon atoms which is free from unsaturated bonds other than aromatic bonds, a divalent mono- or bis-heterocyclic radical with 2 to 10 carbon atoms, or a divalent organic radical with 4 to 20 carbon atoms which consists of more than one said divalent hydrocarbon radical bonded to one another via —O—, —S—, —CO— or —SO₂—, R' represents a divalent hydrocarbon radical with 1 to 20 carbon atoms or a divalent radical with 4 to 20 carbon atoms which consists of more than one hydrocarbon radical bonded to one another via —NH— or —O—, Z represents a hydrolysable group, R'' represents a monovalent radical with 1 to 6 carbon atoms and x is 0 or 1.

2. Process according to claim 1, in which the molar ratio $$\frac{\text{amino-silane}}{\text{bis-imide}}$$

is from 1 to 2.

3. Process according to claim 1, in which the bisimide contains up to 20 mol % of a monoimide which is a maleimide, N-alkyl- or aryl-maleimide, or a maleimide possessing an acetoxy or acetamido group.

4. Process according to claim 1, in which the reaction is carried out at a temperature of 0° to 100°C in at least a partial solvent for the bis-imide.

5. A composition based on imide group-containing organosilicon compound which comprises a compound of the formula:

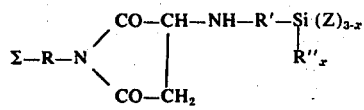

in which R, R', R"Z and x are as defined in claim 1 and Σ represents a radical of the formula:

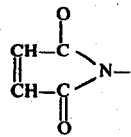

or

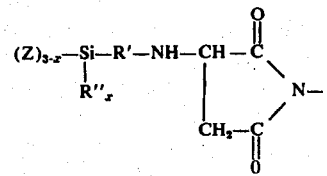

6. A composition according to claim 5, which contains a solvent for the compound.

7. A composition according to claim 5, which contains a curing accelerator.

8. A composition according to claim 5, in which Z represents a group of the formula: —OG,

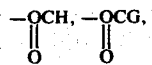

—NHG, —N(G)$_2$,

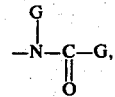

—ON=CHG, —ON=C(G)$_2$, —ON(G)$_2$ in which each of the G radicals, which may be the same or different, represents a monovalent hydrocarbon radical containing at most 15 carbon atoms or two G radicals together form a divalent radical optionally containing a heteroatom.

9. A composition according to claim 8, in which G represents a methyl, ethyl, propyl, hexyl, cyclohexenyl, cyclohexyl, phenyl, benzyl or tolyl radical, or two G radicals form a radical of formula: —(CH$_2$)$_n$ or —(CH$_2$)$_n$—O(CH$_2$)$_n$ in which n is an integer from 1 to 5.

10. In a process for adhering an organopolysiloxane composition which can be vulcanised at ambient temperature in the presence of water in the liquid or vapour state to a substrate which comprises placing an adhesive between the composition and the substrate, the improvement wherein the adhesive is a composition as defined in claim 5.

11. A process according to claim 10, in which the substrate is wood, concrete, a metal, polyethylene, glass or a glass fibre material.

* * * * *